(12) United States Patent
Mulye

(10) Patent No.: US 8,906,419 B2
(45) Date of Patent: Dec. 9, 2014

(54) PHARMACEUTICAL COMPOSITION CONTAINING WATER SOLUBLE DRUG

(75) Inventor: Nirmal Mulye, Princeton, NJ (US)

(73) Assignee: Nostrum Pharmaceuticals, Inc., Edison, NJ (US)

( * ) Notice: Subject to any disclaimer, the term of this patent is extended or adjusted under 35 U.S.C. 154(b) by 0 days.

(21) Appl. No.: 13/012,363

(22) Filed: Jan. 24, 2011

(65) Prior Publication Data

US 2011/0117203 A1    May 19, 2011

Related U.S. Application Data

(62) Division of application No. 10/913,048, filed on Aug. 6, 2004, now Pat. No. 7,897,179.

(60) Provisional application No. 60/492,923, filed on Aug. 6, 2003.

(51) Int. Cl.
    *A61K 9/16*    (2006.01)
    *A61K 31/135*  (2006.01)
    *A61K 9/50*    (2006.01)

(52) U.S. Cl.
    CPC ............. *A61K 9/5078* (2013.01); *A61K 9/5047* (2013.01); *A61K 9/1676* (2013.01)
    USPC ........... 424/490; 514/649; 514/652; 514/653; 514/648

(58) Field of Classification Search
    CPC .. A61K 9/1676; A61K 9/5047; A61K 9/5078
    USPC .......... 424/490; 514/649, 652, 653, 648, 357, 514/211.07
    See application file for complete search history.

(56) References Cited

U.S. PATENT DOCUMENTS

| | | | | |
|---|---|---|---|---|
| 4,096,239 | A | * 6/1978 | Katz et al. | 424/426 |
| 5,213,811 | A | * 5/1993 | Frisbee et al. | 424/493 |
| 5,302,400 | A | 4/1994 | Spios | |
| 5,348,747 | A | * 9/1994 | Bianco | 424/490 |
| 5,362,517 | A | 11/1994 | Flesher et al. | |
| 5,378,528 | A | 1/1995 | Makoui | |
| 5,395,626 | A | * 3/1995 | Kotwal et al. | 424/472 |
| 5,631,248 | A | 5/1997 | Davis et al. | |
| 5,833,891 | A | 11/1998 | Subramaniam et al. | |
| 5,976,696 | A | 11/1999 | Collette et al. | |
| 6,150,556 | A | 11/2000 | Getman et al. | |
| 6,267,985 | B1 | 7/2001 | Chen et al. | |
| 6,294,192 | B1 | 9/2001 | Patel et al. | |
| 6,353,148 | B1 | 3/2002 | Gross | |
| 7,049,000 | B2 | 5/2006 | Fossum et al. | |

FOREIGN PATENT DOCUMENTS

| | | |
|---|---|---|
| JP | 6-256169 A | 9/1994 |
| JP | 7-505644 A | 6/1995 |
| JP | 7-173050 A | 7/1995 |
| JP | 7-196477 A | 8/1995 |
| JP | 8-502264 A | 3/1996 |
| JP | 8-509498 A | 10/1996 |
| JP | 9-511489 A | 11/1997 |
| JP | 2001-520663 A | 10/2001 |
| JP | 2002-514588 A | 5/2002 |
| JP | 2003-517470 A | 5/2003 |
| JP | 2003-189796 A | 7/2003 |
| WO | 94/25008 A1 | 11/1994 |
| WO | WO 99/12848 | 3/1999 |
| WO | 99/58109 A1 | 11/1999 |
| WO | 01/37808 A1 | 5/2001 |
| WO | WO 03/103637 | 12/2003 |
| WO | WO 2004/047718 | 6/2004 |

OTHER PUBLICATIONS

Remington's Pharmaceutical Sciences, Eighteenth Edition, 1990, p. 209.
Physicians' Desk Reference, 49 Edition, 1995, p. 2664.

* cited by examiner

*Primary Examiner* — Aradhana Sasan
(74) *Attorney, Agent, or Firm* — Scully, Scott, Murphy & Presser, P.C.

(57) ABSTRACT

The present invention is directed to a process of preparing beads coated with a water soluble drug for incorporation into a pharmaceutical composition comprising: (a) preparing a supersaturated drug solution containing a desired amount of drug, which is completely saturated at a first temperature but which is supersaturated at a second temperature which is below the first temperature; and (b) coating inert beads with the drug solution, said drug solution being maintained at or below the first temperature but above the second temperature, and said beads maintained at a second temperature, wherein the second temperature is less than the first temperature and wherein the solution containing the drug is supersaturated at the second temperature, as well as to the pharmaceutical compositions containing same.

23 Claims, No Drawings

US 8,906,419 B2

PHARMACEUTICAL COMPOSITION CONTAINING WATER SOLUBLE DRUG

RELATED APPLICATION

The present application is a divisional application of copending application having Ser. No. 10/913,048, filed on Aug. 6, 2004 which is claiming benefit of U.S. provisional Application No. 60/492,923 filed on Aug. 6, 2003.

FIELD OF THE INVENTION

The present invention relates to a method for preparing a pharmaceutical composition comprising a highly water soluble drug such as venlafaxine hydrochloride which is coated on a pellet, and the pharmaceutical composition prepared therefrom. This invention also relates to a controlled release formulation of a water soluble drug.

BACKGROUND OF THE INVENTION

Pharmaceutical compositions containing water soluble drugs are well known in the pharmaceutical arts. For example venlafaxine, 1-[2-dimethylamaino-1-(4-methoxyphenyl)ethyl]cyclohexanol, a drug used for treatment of depression is currently being sold in tablet form. In addition, U.S. Pat. Nos. 6,274,171 and 6,403,120, both to Sherman, et al. describe an extended release formulation of venlafaxine hydrochloride in capsule form. As described therein, the venlafaxine hydrochloride is mixed with a formulation aid, such as microcrystalline cellulose and hydroxypropylmethylcellulose and the plastic mass thus formed is extruded, spheronized and dried to provide uncoated spheroids containing the drug. The spheroids are coated with controlled release polymers, such as hydroxypropylmethyl cellulose, in order to provide a controlled release formulation.

This procedure described in the aforementioned patents requires several steps. For example, it requires wet granulation to make a wet mass for extrusion, the mass is then passed through an extruder to make cylindrical rods of proper diameter, and then the rods are then spheronized using a spheronizer to make spheres. The resulting spheres are then dried, sized and coated with the controlled release polymer to obtain a controlled release formulation.

This process described therein has several disadvantages:

First, it requires several steps and is thus labor intensive; the steps, are at a minimum wet granulation, extrusion, spheronization, drying, sizing and coating.

Second, this methodology often does not produce spheres with uniform diameters, which thus may result in lower process yields.

Third, the process requires a formulation aid such as microcrystalline cellulose and hydroxyproplmethyl cellulose, for spheronization, consequently, it is not difficult to prepare beads and/or capsules containing beads having high concentrations of drug thereon.

Fourth, since the process requires a wet granulation step, it may require non-aqueous solvents, such as ethanol which can be hazardous as well as expensive.

The present inventor, however, has found a much simpler and much more efficient method of making pharmaceutical compositions containing venlafaxine hydrochloride and other water soluble drugs which does not require all of the steps described hereinabove.

The present inventor has found that he can eliminate the wet granulation step, the extrusion step and spheronization steps of the prior art by utilizing a supersaturated solution of the water soluble drug with or without other components and coating inert beads with same. If a controlled release formulation is required, the controlled release polymer is contained in a second coating which is coated onto the first coating comprising the water soluble drug and other components, wherein said first coating coats the inert beads.

Another common way to make a pharmaceutical in which the drug is coated onto a bead or pellet is to disperse the drug in a solvent containing a binder dissolved therein and to coat the inert bead with this solution. A fluidized bed coating method is commonly used to effect this type of coating. To effect coating of the beads with the drug, the drug precipitates or crystallizes out of the solution as the solvent is removed. If the drug does not precipitate out of the solution, it forms a very sticky coating which makes drug loading almost impossible. The presence of a binder, which provides binding and/or stickiness, only worsens the situation. Moreover, if the drug is highly water soluble, the drug does not easily precipitate out of solution. Thus, heretofore no one has extended the use of this methodology for coating water soluble drugs on a bead or pellet.

However, the present inventor has overcome this problem and found a way to coat pellets by modifying this method.

SUMMARY OF THE INVENTION

The present invention is directed to A process for preparing beads coated with a water soluble drug for incorporation into a pharmaceutical composition comprising:
  (a) preparing a supersaturated drug solution containing a desired amount of drug, which solution is completely saturated at a first temperature but which is supersaturated at a second temperature which is below the first temperature; and
  (b) coating inert beads with the drug solution, said drug solution being maintained at or below the first temperature but at or above the second temperature, and said beads being maintained at a second temperature, wherein the second temperature is less than the first temperature and wherein the second temperature is the temperature at which the solution containing the drug is supersaturated. The present invention is also directed to a process of preparing a pharmaceutical composition comprising a water soluble drug which comprises preparing a solution comprising said drug and an aqueous solvent which becomes supersaturated at a coating temperature, and coating said supersaturated solution onto inert beads and formulating a pharmaceutically effective amount into a solid unit dosage form. Another embodiment of the present invention is directed to the pharmaceutical composition thus prepared. A further embodiment of the present invention is directed to a solution which is supersaturated at room temperature comprising a water soluble drug and an aqueous solvent, said water soluble drug being completely dissolved in said aqueous solvent. A further embodiment of the present invention is directed to a method of preparing a controlled release formulation of the water soluble drug, said method comprising preparing a supersaturated solution comprising said water soluble drug and an aqueous solvent, and coating said supersaturated solution onto inert beads to form a first coat and then coating the first coat on said beads with a second coat comprising a controlled release polymer, and then formulating a pharmaceutically effective amount of the resulting product into a solid unit dosage form. In a still further embodiment, the present invention is directed to a process for preparing a controlled release formulation of a water soluble drug which comprises preparing any of the aforesaid formulations and then formulating a pharmaceutically effective amount of said formulations into a solid unit dosage form. Another embodiment is directed to the controlled release formulation products thus formed.

A still further embodiment of the present invention is directed to a process for preparing a pharmaceutical composition comprising a water soluble drug which comprises preparing a supersaturated solution comprising said drug in an aqueous solvent and mixing with a water soluble additive which reduces the solubility of the drug in the aqueous solvent and coating said resulting mixture onto inert beads and formulating a pharmaceutically effective amount into a solid unit dosage form. Another embodiment is directed to the product thus formed. A further embodiment of the present invention is directed to a supersaturated solution comprising a water soluble drug, an aqueous solvent and water soluble additive reducing the solubility of the drug in said solvent, said water soluble drug, and said additive being completely dissolved in said aqueous solvent. A further embodiment of the present invention is directed to a method of preparing a controlled release formulation of a water soluble drug, said method comprising preparing a supersaturated solution comprising said water soluble drug, in an aqueous solvent and mixing with a water soluble additive which reduces the solubility of the drug in the aqueous solvent and coating said mixture onto pellets or beads to form a first coat thereon, and then coating the first coat on said beads with a second coat comprising a controlled release polymer and then formulating a pharmaceutically effective amount of the resulting product into a solid unit dosage form. A further embodiment of the present invention is directed to the various controlled release pharmaceutical compositions thus formed. A still further embodiment of the present invention is directed to a method of preparing a controlled release formulation of a water soluble drug and said method comprising preparing and mixing a supersaturated solution comprising said water soluble drug with an aqueous solvent, a water soluble additive that reduces the solubility of the drug and the aqueous solvent and a controlled release polymer, and coating said mixture onto the inert beads and then formulating a pharmaceutically effective amount of the resulting product into a solid unit dosage form. Finally, another embodiment of the present invention is directed to the product thus formed.

DETAILED DESCRIPTION OF THE INVENTION

As indicated hereinabove, the present formulation comprises a pharmaceutical composition in unit dosage form. The term "unit dosage form," as employed herein, refers to a physically discrete unit suitable as unitary dosage to mammals, including humans, with each unit containing a predetermined quantity of active material calculated to produce the desired effect in association with the carrier and other ingredients in the formulation, as described herein.

A "solid" unit dosage form refers to the unit dosage form being formulated into a solid for administration such as a tablet, capsule, encapsulated bead, and the like.

As used herein, by use of the term "mammal", it is meant a vertebrae of the class mammalia that is characterized by possession of hair and mammary glands. Examples include, inter alia, dog, cat, horse, pig, goat, cow, monkey, human and the like. The preferred species of mammal to which the formulation of the present invention is to be administered is man.

The term "controlled release", as used herein refers to the release of the active ingredients, i.e., the drug, at such a rate that blood levels thereof are maintained within a therapeutic range, but below toxic levels over an extended period of time, e.g., 4 to 24 hours or longer.

As used herein, the term "beads" is synonymous with spheroids, pellets, microspheres, granules, particles, prills, nonpareils, seeds and any like synonymous term used in the pharmaceutical industry used to connote the same.

In accordance with the procedures described herein, various pharmaceutical compositions comprising a water soluble drug can be prepared in unit dosage form.

The drug or medicament that is utilized in the present invention is one that is soluble in water at room temperature. As used herein, the term "drug or medicament that is water soluble" refers to a drug or medicament that has a solubility greater than or equal to about 0.200 grams per 1 gram of water at room temperature (25° C.). Preferred drugs and medicaments have a solubility greater than or equal to 0.300 grams per gram of water at 25° C. and more preferably greater than or equal to 0.400 grams per gram of water at 25° C. and most preferably greater than or equal to 0.500 grams per gram of water at 25° C. Examples of water soluble drugs include venlafaxine•HCl, Metoprolol Tartarate, Diltiazem salts, Pseudoephedrine salts, Phenyltolaxamine, Brompheniramine maleate, Diphenhydramine, and the like. The most preferred drug is venlafaxine HCl.

In preparing the pharmaceutical composition of the present invention, the drug is dissolved in an aqueous solvent. The aqueous solvent may be water or other water based fluid, e.g., buffers, or any other aqueous solvent normally used in water soluble pharmaceutical compositions in which a water soluble drug is soluble or a water soluble organic solvent, such as alcohol, e.g., methanol, ethanol, isopropanol, acetone, and the like. The most preferred aqueous solvent is water.

The water that is used in dissolving the drug or medicament is water that is normally used in the pharmaceutical arts. It may be tap water or spring water, but it is preferred that the water is deionized or distilled water. It is more preferred that it is sterile. Since a supersaturated solution of water soluble drug is utilized in accordance with the present process, the amount of drug contained therein is substantial. The supersaturated solution may contain as much as about 70% by weight drug or more. The supersaturated solution may contain at least about 30% by weight drug or it may contain at least about 40% by weight drug or it may contain at least about 50% by weight drug or it may contain at least about 60% by weight drug.

In accordance with the present invention the water soluble drug is dissolved in an aqueous solvent at a first temperature. Although it may be an aqueous based solvent, such as a buffer, and the like, it is preferred that the aqueous solvent is water. The drug is dissolved in the aqueous solvent at a first temperature. As used herein, the first temperature is the saturation temperature. The first temperature is dependent upon the amount of drug desired to be utilized as well as the solubility of the drug in water. Since the aqueous solvent can only dissolve a certain amount of drug at a given temperature, if more than that amount is desired, then the aqueous solvent containing the drug is heated to a higher temperature. Preferably, the first temperature ranges from just below ambient temperature to just below the boiling temperature of water, e.g., from about 15° C. to about 90° C., but more preferably ranges from about 25° C. to about 80° C., and more preferably from about 30° C. to about 60° C. and most preferably from about 35° C. to about 50° C. In accordance with the present invention, the drug dissolved in the aqueous solvent become supersaturated at a second temperature which is lower than the first temperature. As used herein, the second temperature is the temperature of the supersaturated solution. The second temperature in an embodiment of the present invention ranges from about 2° C. to about 15° C. below the first temperature. In one embodiment it is about 2° C. to about 5° C. below the first temperature. In another embodiment, it ranges from about 11° C. to about 15° C. below the first temperature. In a third embodiment, the second temperature is greater than about 15° C. below the first temperature. For example, the second temperature in one embodiment is less than about 30° C. but greater than about 0° C., and more preferably it ranges from about 20° C. to about 25° C. In another embodiment it is less than about 20° C. The coating of the beads occurs at a third temperature, the coating temperature or product temperature which is below the first temperature but at or above the second temperature.

The following exemplifies the process. In accordance with the present invention a drug solution is prepared in an aqueous solvent, water in most cases, at a concentration higher than the saturation concentration at about room temperature (25° C.). Such a solution is prepared by either suspending the drug in the solvent and heating until it is completely dissolved or by adding the drug to the solvent which is previously heated. The solvent is heated to a temperature slightly higher than the saturation temperature. As used herein, the term saturation temperature is the minimum temperature required to dissolve a desired quantity of the drug in the aqueous solvent. Any additives added thereto are dissolved after all of the drug has been added. The solution thus prepared is allowed to cool down during the coating process. Preferably, the saturated solution is cooled slowly. If cooled sufficiently slowly, the drug and any other additional ingredients dissolved in the heated solution remain dissolved in the solution. This would bring the temperature of the solution below the saturation temperature, thus forming a supersaturated solution. This solution is sprayed onto inert beads maintained at a temperature lower than the saturation temperature (the temperature of the beads is called the "product temperature"), which is lower than the saturation temperature but at or greater than the supersaturation temperature. Preferably, the product temperature is about room temperature (about 20 to about 25° C.). Preferably, the solution is sprayed onto the beads using a coating machine such as a fluid bed coating machine, which contains an air jet from which a stream of air is directed onto the beads. Preferably, the beads are cooled at about room temperature (about 20 to about 25° C.) using the inlet air of the air jet.

Without wishing to be bound it is believed that as the solution is sprayed onto the beads, the evaporation of water, the atomizing air as well as the flowing inlet air, causes the solution to cool down. When the spray droplets come in contact with the beads maintained at a temperature lower than the saturation temperature, the droplets of the solution cool further. Consequently, as a result, a much higher degree of supersaturation is achieved, causing the drug to crystallize/precipitate onto the surface of the beads, and thereby causing the beads to be cooled with the drug. The coat thus achieved using this method is not sticky and produces drug loaded beads which are free of binders. The inventor has also found that if coating is carried out at the proper temperatures, binders can be added without making the coating process difficult or impossible.

The temperatures utilized are critical in this process. If the coating temperature occurs at the saturation temperature, the product becomes wet and becomes sticky making the coating process very difficult or impossible because it is very difficult to maintain fluidization if the beads stick to each other.

As used herein the term "inlet temperature" is the temperature of the inlet air flowing into the coating machine.

The "product temperature" is the temperature of the product or the beads during the coating operation. It is also called the "coating temperature" herein and the "third temperature". This temperature is usually slightly below the inlet temperature while the coating process is taking place because of the cooling caused by the evaporating solvent.

"Saturated solution" as used herein, refers to a solution containing drug at a concentration at a maximum solubility of that drug in that solvent.

A "supersaturated solution" is a solution containing drug at a concentration higher than the saturation concentration. The term "supersaturated solution" in the text refers to the solution which is at a higher concentration than the saturation concentration of the drug at the supersaturated temperature.

The "saturation temperature" as used herein is the temperature at which the solution becomes a saturated solution at a given concentration of the drug. In the case of a supersaturated solution, increasing the temperature would increase the solubility of the drug and at a certain temperature, the solution would lose supersaturation and concentration would become equal to the saturation concentration at that temperature. This temperature is called the saturation temperature. A solution which is not a saturated solution but above the temperature at which saturation takes place could be cooled down to a temperature where it will become saturated.

A "highly water soluble drug" is a drug with a solubility greater than 100 mg per gram of water at room temperature.

Since it is most convenient (convenient because it is easier to regulate the temperature of the inlet air) to maintain the inlet air temperature at or higher than the room temperature, it is important that the saturation temperature is significantly higher than the inlet temperature. Most preferably, a solution of the drug at a concentration higher than the saturation concentration at room temperature is prepared by dissolving the drug with the aid of heat. The coating process is carried out with the inlet air temperature which is preferably near room temperature. If the drug is thermolabile (heat sensitive), it can be dissolved in the solvent at room temperature to form a saturated solution and the coating process is carried out at a temperature lower than the room temperature using chilled inlet air.

The beads thus produced can be further coated with a second coat comprising a controlled release coating using water insoluble materials such as polymers or waxes in amounts sufficient to achieve controlled release of the drug. In another embodiment, the drug loaded beads are coated with a protective coat between the drug layer and the controlled release coat to prevent incompatibilities or migration of the drug into or onto the controlled release coating. In another embodiment, a protective coat is placed over the controlled release coat. In a still further embodiment, the beads are coated with a protective coat between the drug layer and the controlled release coat and a protective coat is placed over the controlled release coat. These protective coats are comprised of components normally found in pharmaceutical compositions.

As described hereinabove, a supersaturated solution containing the drug is prepared. The supersaturated solution contains an amount of water soluble drug greater than its saturation concentration at room temperature. Unless indicated to the contrary, the term "saturation concentration" is the percent by weight of a solution of the maximum amount of a drug that could be dissolved in 1 gram of water at room temperature. For example, venlafaxine•HCl is a highly water soluble drug with about 0.567 grams being soluble in 1 gram of water at room temperature. In short, about 33% solution of venaflaxine•HCl in water is considered as a saturated solution. Thus, the supersaturated solution of venaflaxine•HCL used in the present invention contains at least about 33% (w/w) solution of the drug.

Each drug has its own saturation concentration in water. If it is not known, it can be determined by conventional methods. For example, a known amount of the water soluble drug is added to a container of known weight, containing 1 gram of water at a desired temperature, e.g., room temperature. As more and more water soluble drug of known amount is added to the water, there will be a point when no more drug will dissolve. At this point, the aqueous solvent cannot hold any more drug, and the excess drug will fall to the bottom of the container and remain as a solid. The excess solid is separated from the water by techniques known in the art, such as by decanting, filtering and the like; the separated solution contains the saturated solution of the drug at the desired temperature, for example, room temperature. The amount or concentration of the drug in the solution is determined by analytical techniques known in the art. For example, if a known amount of drug is added to the water and the amount (dry weight) of the drug that is in excess is subtracted out, the difference is the amount of drug soluble in the solution at the given temperature. Thus, the saturation concentration is the weight percentage of the water soluble drug to the total weight of the drug and water.

As indicated hereinabove, the amount of drug used in preparing the pharmaceutical composition of the present invention is greater than the saturation concentration of the drug at room temperature. The supersaturated solution of a drug is prepared by conventional techniques known to prepare supersaturated solution in general. For example, the desired amount of drug is added to the aqueous solvent and the mixture is heated to a temperature higher than the saturation temperature where the drug completely dissolves. Alternatively, the solvent is heated to a temperature higher than the saturation temperature required for the desired concentration of the drug, and the drug is added to form a solution. The heated solution is then allowed to cool at a rate sufficiently slow so that the added drug in excess of the saturation concentration remains in solution when cooled to below the first temperature, e.g., to room temperature; as a result, the solution becomes supersaturated at a temperature lower than the first temperature. The additives are added after the drug is completely dissolved. Thus, the drug solution is cooled due to dissolution of these ingredients and the solution is therefore supersaturated. The temperature in which the excess water soluble drug present in the water at a concentration above the saturation concentration of the drug at room temperature becomes dissolved is designated herein as the "saturation temperature". As understood by one of ordinary skill in the art, the greater the amount of drug to be added to the solution, the greater is the saturation temperature; in other words, the saturation temperature is a function of the amount of water soluble drug present. The supersaturated solution is allowed to cool to a temperature below the saturated temperature, at which temperature, (the "second temperature" or supersaturated temperature") the supersaturated solution is maintained. It is preferred that the supersaturated solution is maintained at or below room temperature.

The pharmaceutical composition of the present invention is prepared by coating a core comprising inert beads with the supersaturated solution comprising the drug and aqueous solvent prepared at or greater than the first temperature (saturation temperature) and the core is maintained at a second temperature (product temperature) which is below the first temperature. The term "core", as used herein, refers to any inner core which is known in the art to be suitable for use in pharmaceutical coating technology, e.g., granules or beads made of sugars or sugar alcohols (such as sucrose, lactose, mannitol, xylitol, and the like), cellulose, such as microcrystalline cellulose and the like, starch or any free flowing non friable granular material which does not chemically react with pharmacology active substances. It is preferred that the core is a sugar or starch sphere having an average diameter of from about 0.1 mm to about 1.5 mm.

The inert material of the core acts as an inert carrier. It is physically separate from the drug coating. It is not a formulation aid ultimately mixed with drug to permit spheronization.

To the supersaturated solution comprising the water soluble drug and the aqueous solvent may be added additional water soluble ingredients described hereinbelow. The supersaturated solution contains an amount of the water soluble drug that is greater than its saturation concentration at 25° C. The saturation temperature is dependent upon the amount of drug desired to be present in the product The amount of the water soluble drug present therein may be as little as 1% greater by weight than the saturation concentration of the water soluble drug in water at 25° C. or as much as 150% greater by weight than the saturation concentration of the drug in water at 25° C. or any amount therebetween. However, it is preferred than the amount of drug present is at least 10% greater and more preferably at least 20% greater than the saturation concentration and more preferably at least about 50% greater than the saturation concentration and even more preferably at least about 100% greater than the saturation concentration. On the other hand, it is preferred that the concentration of the water soluble drug is at most 200% greater than the saturation concentration and more preferably at most double that of the saturation concentration of the water soluble drug in water at 25° C.

The supersaturated solution is prepared by thoroughly mixing the desired amount of drug in excess of the saturation concentration in the aqueous solvent with the other ingredients present in the first coat. Although the aqueous solution may be heated up to the boiling point of the aqueous solvent, e.g., 100° C., if the aqueous solvent is water, it is preferred that the mixture is heated up to at most about 80° C. and more preferably to at most about 60° C. and even more preferably at most about 50° C. It may be heated as low as about 40° C. or less (but above room temperature) or may be heated up to 35° C. or more. The solution is cooled slowly to a temperature lower than the temperature used for heating. It is preferred that the supersaturated solution is maintained at about room temperature. The solution may be maintained at a temperature higher than room temperature, or it may be maintained at or near the saturation temperature.

The supersaturated solution itself may be used for coating the core. Alternatively, the supersaturated solution thus formed may be mixed with any other desired components normally used in the pharmaceutical compositions and the resulting product coats the core. Regardless, of which is used, the techniques for coating the core is the same. Thus, the procedure described herein will refer to coating the core with the supersaturated solution, but it is to be understood that the procedure is also applicable to a mixture comprising the supersaturated solution of the drug with any other pharmaceutical ingredients normally present in a coat. Moreover, it is to be understood that the mixture of additional components is to be added to the supersaturated solution of the water soluble drug prior to coating the core.

The coating is effected using conventional techniques known in the art. For example, the core may be coated with the supersaturated solution in a fluidized bed or pan coating. Other examples include spraying the supersaturated solution onto the core. It is preferred that the coating is effected using a fluidized bed coating system. Moreover, the beads are maintained at a temperature lower than that of the supersaturated solution or resulting product, e.g., the beads are maintained at a temperature of less than room temperature, e.g., the product temperature.

Various conventional fluidized bed coating apparatus may be employed, for example, a fluidized bed coating apparatus or a fluidized bed granulating coating apparatus. In the processes described herein, it is to be understood that during the coating of the core, the solvent, e.g., water, is removed.

Without wishing to be bound, it is believed that the beads are dried as a result of the energy imparted due to the atomization into small droplets and to the inlet airflow. Moreover, it is believed that the cooling of the beads occurs due to evaporation of the solvent. The simultaneous drying and cooling causes the drug to precipitate and form the coat on the beads.

In one example, the supersaturated solution is coated onto the core using a Wurster type fluid bed system. A Wurster fluidized-bed system is one in which an air jet, injected from underneath, fluidizes the core and effects drying while the coating is sprayed. In such a system, the fluidized bed coating vessel includes a bottom air inlet nozzle and a top or upper air outlet nozzle. The vessel typically has a divergent middle body expansion section, and an air distribution plate spans the vessel. The distribution plate defines an upper reactor section or a lower feed section or air or inlet plenum. The distribution plate includes orifies therein to effect a relatively even air distribution across the plate.

In one embodiment, a partition-like, cylindrical coating column extends upwardly from above the distributor plate into the reactor section. The space between the coating column and the vessel walls define a downflow bed. The coating column is positioned above the distribution plate to define a gap therebetween. The gap is sized to permit the inflow of material from the downflow bed, through the gap and into the column. A spray nozzle extends from the feed section into the coating column from below the distribution plate. The spray nozzle extends from the feed section into the coating column from below the distribution plate. The spray nozzle is configured to provide a spray of coating material into the column.

In operation, the vessel is charged with a quantity of inert cores, e.g., beads, to be coated. The inert cores rest in the down flow bed, above the distribution plate and surrounding the coating column.

Air is supplied to the vessel through the air inlet nozzle, into the inlet plenum. The air flow rate is selected to fluidize the downflow bed. In a typical arrangement, the airflow is selected to establish an incipiently fluidized bed in the region surrounding the coating column. In the incipiently fluidal bed, the pressure drop across the bed is equal to the gravitational force acting on the beads. Thus, the bed is minimally fluidized and no voids or channels are formed therein.

The supersaturated solution of the drug and other desired ingredients described hereinabove are fed into the coating column through the spray nozzle. The upward flow of material and air through the column create a low pressure zone at the bottom thereof which draws the beads from the downflow bed, through the gap between the distributor plate and the column. As the beads enter the column, they are accelerated upwardly, by the spray and air flow.

In the coating column and the space thereinabove, the beads are sprayed (or wetted) by intimate mixing of the beads and the supersaturated solution. As the coated beads rise in the column and lose energy, they are forced outward, away from the upward flow stream above the column. When the beads lose sufficient energy to be overcome by gravitational forces, they fall back down onto the downflow bed. The process is continued until the entire batch of charged beads is coated. Then the process is complete, the beads are removed from the vessel for further processing. In some fluidized bed coating systems, a significant amount of drying of the beads occurs within the reactor vessel upper areas prior to the beads falling back into the down flow column.

The coating is applied so as to substantially uniformly and rapidly contact and coat the core. It is preferred that the coating composition has substantially a uniform thickness around the core.

Another example of a fluidized bed coating apparatus that could also be used to coat the supersaturated solution onto the beads is described in U.S. Pat. No. 6,126,967, the contents of which are incorporated by reference.

The particular process controls, flow rate and pressure are typically determined by, among other things, the particle size and density of the beads, the thickness of the coating desired, the conditions of the infed air and the drying requirements. The particular process control parameters for a given system will be recognized by those skilled in the art.

The present inventor has overcome a major problem; as is well known in the art, the extreme high solubility of the drug may create unusual problems because the drug precipitates out only after most of the solvent is evaporated. The bead, as a result, becomes extremely tacky and sticky, thereby making the coating process difficult, if not impossible. The addition of the binder exacerbates the problem. However, the process described hereinabove, however, does not provide a bead that has a sticky and/or tacky coating thereon.

Without wishing to be bound, it is believed that the air flow in the fluidized bed coating apparatus causes water from each droplet of the aqueous solution to evaporate from the supersaturated solution, thereby concentrating the drug in the supersaturated solution. Moreover, it promotes cooling. Thus, the spray droplet forms a supersaturated solution. The beads are maintained at a temperature below that of the supersaturated solution. For example, the supersaturated solution may be maintained at room temperature and the beads are at a temperature below room temperature; as the spray comprising the water soluble drugs hits the core, the drug will crystallize and/or precipitate on contact with the beads.

As indicated hereinabove, besides water and drug, the supersaturated solution may contain other optional components, commonly used in pharmaceutical compositions that are water soluble. These other components are additives normally found in coatings used in the pharmaceutical arts. These optional ingredients include excipients, such as plasticizers and fillers, coloring agents, preservatives (methyl parabens), surfactants, artificial sweeteners, flavorants, anti-oxidants and the like of all of which are preferably soluble in water.

The surfactant utilized is either non-ionic or ionic. It is preferred that the surfactant is non-ionic. Moreover, the surfactant utilized may be a hydrophilic surfactant. It is even more preferred that the surfactant is hydrophilic and non-ionic.

The surfactant is present in effective concentration. It is preferred that, if present, it is present in an amount ranging from about 0.01 to about 5% by weight and more preferably from about 0.1% to about 3% by weight of the pharmaceutical composition.

A suitable hydrophilic surfactant will generally have an HLB value of at least 10. As is well known, surfactants must necessarily include polar or charged hydrophilic moieties as well as non-polar lipophilic moieties, that is, a surfactant must be amphiphilic. An empirical parameter commonly used to characterize the relative hydrophilicity and hydrophobicity of non-ionic amphiphilic compounds is the hydrophilic lipophilic balance ("HLB value"). Surfactants with lower HLB values are more lipophilic and have greater solubility in aqueous solutions. Hydrophilic surfactants are generally considered to be those compounds having an HLB value greater then about 10, as well as an ionic, cationic or zwitterionic compounds for which an HLB scale is not generally applicable.

The Hydrophilic surfactants used in the present invention may be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acyl lactylates; mono- and di-acetylated tartaric acid esters of mono- and di-glycerides; succinylated mono- and di-glycerides; citric acid esters of mono- and di-glycerides; and mixtures thereof.

Within the aforementioned group, preferred ionic surfactants include, by way of example: the ionized from a surfactant selected from the group consisting of: lecithins, lysolecithin, phospholipids, lysophospholipids and derivatives thereof; carnitine fatty acid ester salts; salts of alkylsulfates; fatty acid salts; sodium docusate; acyl lactylates; mono- and di-acetylated tartaric acid esters of mono- and di-glycerides; succinylated mono- and di-glycerides; citric acid esters of mono- and di-glycerides; and mixtures thereof.

More preferred ionic surfactants are the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof. The preferred ionic surfactant is sodium lauryl sulfate.

Preferred hydrophilic non-ionic surfactants include alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof; polyoxyethylated vitamins and derivatives thereof; polyoxyethylene-polyoxypropylene block copolymers; and mixtures thereof.

More preferably, the hydrophilic non-ionic surfactant is selected from the group consisting of polyethylene glycol sorbitan fatty acid esters and hydrophilic transesterification products of a polyol with at least one member of the group consisting of triglycerides, vegetable oils, and hydrogenated vegetable oils. The polyol is preferably glycerol, ethylene glycol, polyethylene glycol, sorbitol, propylene glycol, pentaerythritol, or a saccharide.

Examples of hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 40, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10oleate, Tween 40, Tween 60, sucrose monostearate, sucrose monolaurate, sucrose monopalmitate, PEG 10-100 nonyl phenol series, PEG 15-100 octyl phenol series, and poloxamers.

Among these preferred non-ionic surfactants, more preferred are PEG-20 laurate, PEG-20 oleate, PEG-35 castor oil, PEG-40 palm kernel oil, PEG-40 hydrogenated castor oil, PEG-60 corn oil, PEG-25 glyceryl trioleate, polyglyceryl-10 laurate, PEG-6 caprate/caprylate glycerides, PEG-8 caprate/caprylate glycerides, PEG-30 cholesterol, polysorbate 20, polysorbate 80, POE-9 lauryl ether, POE-23 lauryl ether, POE-10 oleyl ether, PEG-24 cholesterol, sucrose monostearate, sucrose monolaurate and poloxamers. Most preferred are PEG-35 castor oil, PEG-40 hydrogenated castor oil, PEG-60 corn oil, PEG-25 glyceryl trioleate, PEG-6 caprate/caprylate glycerides, PEG-8 caprate/caprylate glycerides, polysorbate 20, polysorbate 40, polysorbate 80, tocopheryl PEG-1000 succinate, PEG-24 cholesterol, and hydrophilic poloxamers.

The surfactant, when present, is present in effective concentration. It is preferred that if present it is present in an amount ranging from about 0.01% to about 5% by weight and more preferably, from about 0.1% to about 3% by weight of the pharmaceutical composition.

The coloring agents are added to provide elegance and product distinction. Suitable ingredients for providing color to the formulation include titanium dioxide and color pigments, such as iron oxide pigments, FD&C Yellow No. 6, FD&C Red No. 2, FD&C Blue No. 2, food lakes and the like.

The plasticizer may be selected from those plasticizers normally used in coating compositions of pharmaceuticals. Examples include diethylphthalate, triethyl citrate, triethyl acetyl citrate, triacetin, tributylcitrate, polyethylene glycol, glycerol, vegetable and mineral oils, maltodextrin and mixtures thereof, and the like. It will be understood that the plasticizer used may be present in the coating in amounts ranging from about 0.01% to about 25% by weight and more preferably from about 5 to about 15% by weight based on the dry weight of the coating.

The coating layer may optionally include a lubricant, especially if compressed into a tablet. Examples of suitable lubricants include talc, calcium stearate, colloidal silicon dioxide, glycerin, magnesium stearate, aluminum stearate or a mixture of any two or more of the forgoing, and the like. If present, the lubricant is present in amounts ranging from about 0.01% to about 10% by weight based on the dry weight of the coating.

With most other drugs made by fluid bed processor, a binder is necessarily present along with the drug in order for the drugs to stick to the beads and form a film. However, the inventor has found that due to the high solubility of the drug in water, a high level of tackiness is not noticed. Thus, a binder is not necessary, and need not be added to the pharmaceutical composition of the present invention. However, although not necessary, a binder may nonetheless be present. Binders, like water soluble polymers, strengthen the coat.

Venlafaxine hydrochloride is an example of a water soluble drug that can be coated onto beads using the present method. It is a highly water soluble drug; about 0.567 grams thereof is soluble in 1 gram of water at room temperature. Thus, a saturated solution of venaflaxine•HCl in water is about 33% (w/w). The above procedure enables the preparation of a coating on the inert core to have a concentration of venlafaxine•HCl to be greater than 33% (w/w). In fact, using the above procedures, one can prepare a coating on the inert bead to contain venlafaxine hydrochloride in concentrations greater than about 40% (w/w), even concentrations greater than about 50% (w/w) and even more remarkably concentrations greater than about 60% by weight.

Moreover, the trend is not specific to venlafaxine hydrochloride. Coatings containing other water soluble drugs, as defined herein, can contain drug concentrations therein of greater than about 33% (w/w), or greater than about 40% (w/w), or greater than about 50% (w/w) and even greater than about 60% (w/w).

Besides the optional ingredients discussed hereinabove, a water soluble additive can be added and mixed with the supersaturated solution. This causes the drug to precipitate more easily. Thus, when the supersaturated drug solution containing the water soluble additive comes in contact with the inert core at a temperature below the saturation temperature during the coating process, the coating can be effected at higher drug concentrations and greater coating can be effected.

It is preferred that the pharmaceutical composition contains a water soluble additive. The water soluble additives reduce the solubility of the drug in water. Preferably, the water soluble additive is a water soluble polymer. Examples include polyethylene glycol ("PEG"), as well as water soluble solvents especially water soluble volatile solvent such as methanol, ethanol, isopropanol, acetone and the like. It is preferred that the water soluble additive is PEG or a combination of PEG and a second water soluble polymer. The polyethylene glycol may be a liquid or a solid. In a preferred embodiment, the PEG has a degree of polymerization greater than about 800. In another embodiment, the polyethylene glycol has a degree of polymerization greater than about 1400, while in a more preferred embodiment, the PEG has a degree of polymerization greater than about 3000 and even as high as about 4000.

The water soluble additive is added to the supersaturated solution in amounts effective to reduce the solubility of the water soluble drug in water. In a preferred embodiment, the water soluble additive is present, on a dry weight basis, at a concentration ranging from about 2% to about 50%, more preferably from about 2% to about 40% (w/w) and more preferably ranging from about 5% to about 30% by weight and even more preferably from about 10% to about 25% by weight and most preferably at about 20% by weight.

Controlled release formulations can also be prepared. By "controlled release", it is meant that either the release of the drug is delayed until after the drug passes through the stomach, or the drug is released over a prolonged period of time as a sustained release pharmaceutical or both.

The controlled release polymer may be present as a film on the first coat comprising one or more controlled release polymers. A second layer is coated on the first layer described hereinabove with sufficient amount of controlled release polymer to release the drug in an aqueous solvent at the desired rate. In this embodiment, the controlled release formulation comprises the inert core, as described hereinabove, an inner layer comprising the water soluble drug, optionally the water soluble additive and an outer core comprising the controlled release polymer. This formulation may optionally contain in either the first or second coat or both any other component that is normally present in sustained release polymers. The controlled release polymer for coating may be an aqueous latex dispersion or a solution in an organic solvent system.

Optionally, there may be another coat present separating the drug layer and the controlled release coat. Alternatively, there may be a coat on top of the controlled release coat. In another embodiment, both of these coats are present in the pharmaceutical composition.

The controlled release polymer herein refers to a polymer that controls the active ingredient to be released in a suitable amount. The polymer may be any controlled release polymer that is conventionally used in the art for preparing controlled release dosage forms. Examples of such polymers include, but not limited to, water insoluble polymers, water soluble polymers, enteric polymers, and the like, and mixtures thereof.

Water insoluble polymers suitable for use in the invention include, but not limited to, cellulose derivatives, such as ethylcellulose; acrylic polymers, such as polyacrylamide, polyacrylic dextrin, polyalkylcyanoacrylates, polymethyl-methacrylates and methacrylic resins; polyvinyl acetate; polyvinyl chloride; polyethylene; and the like; and mixtures thereof. Preferably, the water insoluble polymer used in the invention is ethylcellulose.

In the invention, if present, the water insoluble polymer preferably comprises about 2% to about 30% by weight, more preferably about 4% to about 25%, and most preferably from about 6% to about 20% by weight of the pharmaceutical composition.

Water soluble polymers suitable for use in the invention include, but not limited to, hydroxypropylcellulose, hydroxypropylmethylcellulose ("HPMC"), carboxymethylcellulose, xanthan gum, polyvinylpyrrolidone ("PVP") and the like, and mixtures thereof, e.g., hydroxypropyl methyl cellulose and xanthan gum. Preferably, the water soluble polymer used in the invention is hydroxypropylcellulose or hydroxypropylmethylcellulose. More preferably, the polymer is hydroxypropylmethycellulose. If present, the water soluble polymer is present in an amount preferably ranging from about 0.01% to about 8% by weight, and more preferably from about 0.1 to about 4% by weight and most preferably from about 0.25 to about 2% by weight of the pharmaceutical composition.

Enteric polymers suitable for use in the invention include, but not limited to, cellulose acetate phthalate, hydroxypropylmethylcellulose acetate succinate, carboxymethylcellulose, styrene acrylic copolymers, methacrylic copolymers, maleic anhydride copolymers, shellac, and the like, and mixtures thereof. If present, it is preferably present in about 2% to about 30% by weight of the pharmaceutical composition, more preferably from about 4% to about 25% by weight and most preferably from about 6% to about 20% by weight of the pharmaceutical composition.

In accordance with the invention, the release-controlling polymer may comprise one or more of the above described polymers. For instance, the water soluble polymer may be used alone. In one embodiment of the invention, ethylcellulose is used alone or in combination with another water soluble polymer, enteric polymer or insoluble polymer. The water insoluble polymer may be used in combination with another water insoluble polymer, enteric polymer or water soluble polymer. Finally, the enteric polymer may be used in combination with another enteric polymer, water soluble polymer or water insoluble polymer. The water soluble polymer may also be used in combination with a water insoluble polymer. In another embodiment of the invention, ethylcellulose is used in combination with hydroxypropylcellulose or hydroxypropylmethylcellulose. In addition, the enteric polymer may also be used alone. In a further embodiment of the invention, shellac is used alone. Furthermore, it is possible to use two polyacrylates. A still further embodiment of the invention uses the combination of acrylic acid and a methacrylate polymer. The controlled release polymer coatings can be an organic solvent or aqueous latex based dispersion.

The amount of release-controlling-film-forming polymer in the controlled release dosage form of the invention should be sufficient to effectively control the drug to be released in a desired amount at a derived rate.

The release-controlling layer of the controlled release dosage form of the invention may further comprise one or more plasticizing agent.

The platicizing agent used herein refers to any organic molecule capable of increasing the flexibility and toughness of final products by internally modifying or solvating polymer molecules. Plasticizing agents suitable for use in the invention include, but not limited to, phthalates, such as dibutyl phthalate; adipates; sebacates, such as dibutyl sebacate; ethylene glycol; polyethylene glycol and their derivatives; tricresyl phosphate; castor oil; citrates, such as triethyl citrate, tributyl citrate, acetyl tributyl citrate; triacetin; acetylated mono-, di- and triglycerides; and the like; and mixtures thereof. Preferably, the plasticizing agent used in the invention is selected from the group consisting of dibutyl phthalate, dibutyl sebecate and triethyl citrate.

The second coat, if present, is preferably coated onto the first layer which contains the active ingredient using conventional techniques in the art, such as by fluid-bed coating or pan coating. The components in the second coat comprising the sustained release polymer are formulated into a coating solution with a suitable aqueous solvent, such as water, a mixture of water and an organic solvent or a mixture of organic solvents or an aqueous dispersion.

Suitable organic solvents are those customarily used in the art, e.g., alcohols, such as ethanol, propanol or isopropanol; ketones such as acetone; and chloroalkanes, such as methylene chloride.

To facilitate the processing, one or more conventional pharmaceutically acceptable excipients and additives can be added to the first coat and/or second coat, e.g., anti-foam agents, filler, coloring agent, flavoring agent, perfumes, sweetening agents, surface active agents, lubricants, stabilizing agents, anti-tacking agents, and the like, or mixtures thereof.

For instance, one or more anti-tacking agents can be used in the coating solution to uniformly disperse the components. Anti-tacking agents suitable for use in the invention are those customarily used in the art, which include, but not limited to, polymeric electrolytes, condensed silicates, polyphosphates, xylin derivatives, such as aluminum stearate, aluminum laurate, magnesium stearate, calcium stearate, zinc stearate, talc, kaolin, fumed silica, and the like, and mixtures thereof. Preferably the anti-tacking agent is talc or silica, which also acts as a light-barrier.

The pharmaceutical compositions comprising beads, the first coat thereon, and optionally the second coat, if present, are formulated into tablets or capsules or other desired solid unit dosage form by conventional techniques known in the art. If it is a tablet, it can be any suitable shape, such as round, oval, bioconcave, hemopherical or a polygonal shape, such as square, rectangular, pentagoral and the like.

The beads produced using the above-identified techniques are highly spherical and uniform. Since the beads can be coated to almost any extent, beads with high drug concentrations can be easily made. This allows the reduction of the size of the dosage form for high dose drugs. If the beads are made with higher concentrations of drug, less coating is needed for controlled release because of the reduced specific surface area. The smooth surface thus formed by the process also adds to the efficiency of the controlled release coating layer.

This process described herein produces uniformly coated beads. If sustained release formulations are prepared, the controlled release coated product prepared in accordance herewith is much more reproducible and less variable in terms of the release rate.

As used herein, the plural denote the singular and vice versa. The terms "controlled release polymer" and "sustained release polymer" are synonymous and are used interchangeably. Moreover, the term "layer" and "coat" are synonymous as used herein, and are used interchangeably.

The following non-limiting examples further illustrate the present invention.

EXAMPLE 1

Venlafaxine•HCl (1.5 g) was dissolved in water (1.0 Kg). The drug was dissolved in water with slight heating at about 50° C. The supersaturated drug solution was sprayed onto sugar beads (sugar sphere #20/25; 1.5 kg) using a fluid bed coater under the following conditions:

| | |
|---|---|
| Inlet Air Temperature | 30° C. |
| Product Temperature | 22-25° C. |
| Atomization Air Pressure | 3 Bar |

EXAMPLE 2

Venlafaxine hydrochloride (1.5kg) was dissolved in water (1.2kg) with slight heating at about 50° C. Polyethylene glycol (PEG 3350, 0.3 Kg) was dissolved in the drug solution. The drug solution was sprayed onto the sugar beads using a fluid bed coater under the following conditions:

| | |
|---|---|
| Inlet Air Temperature | 30° C. |
| Product Temperature | 22-25° C. |
| Atomization Air Pressure | 3 Bar |

EXAMPLE 3

The product of Example 2 was coated with a seal coat using hydroxypropylmethyl cellulose (10% w/w) until there was a 1% weight gain. The seal coated beads were coated using ethyl cellulose aqueous dispersion (15% w/w) until there was a 10% weight gain, with samples being removed after each increment 1% gain in weight.

The resulting products were subjected to dissolution testing. The dissolution testing was carried out using a USP II apparatus in 900 mL of water.

The results are tabulated hereinbelow:

| Time in HRS | % Release in water | | | |
|---|---|---|---|---|
| | 6% wt gain | 7% wt gain | 8% wt gain | 9% wt gain |
| 1 | 22.05 | 19.78 | 15.08 | 12.16 |
| 2 | 43.05 | 37.67 | 30.65 | 23.00 |
| 4 | 71.74 | 66.63 | 66.85 | 47.99 |
| 6 | 82.26 | 77.12 | 76.77 | 59.15 |
| 8 | 90.78 | 85.91 | 82.31 | 70.19 |
| 10 | 95.35 | 91.70 | 88.72 | 76.42 |
| 12 | 99.60 | 96.26 | 91.94 | 82.25 |

EXAMPLE 4

Using the procedure of Example 1 or 2, the following drug solution formulation was prepared.

| Venlafaxine HCl | 1.5 Kg |
|---|---|
| PEG 3350 | 0.225 Kg |
| HPMC | 0.075 Kg |
| Water | 1.2 Kg |

The drug was dissolved in water with slightly heating. PEG was dissolved in the drug solution. The HPMC is dissolved in the drug solution following PEG addition.

EXAMPLE 5

Using the procedure of Example 1 or 2, the following drug solution formulation was prepared.

| Venlafaxine HCl | 1.5 Kg |
|---|---|
| PEG 3350 | 0.15 Kg |
| HPMC | 0.15 Kg |
| Water | 1.2 Kg |

The drug was dissolved in water with slightly heating. PEG was dissolved in the drug solution. The HPMC is dissolved in the drug solution following PEG addition.

EXAMPLE 6

Using the procedure of Example 1 or 2, the following drug solution formulation was prepared.

| Venlafaxine HCl | 1.5 Kg |
|---|---|
| PEG 3350 | 0.075 Kg |
| HPMC | 0.225 Kg |
| Water | 1.2 Kg |

The drug was dissolved in water with slightly heating. PEG was dissolved in the drug solution. The HPMC is dissolved in the drug solution following PEG addition.

EXAMPLE 7

Using the procedure of Example 1 or 2, the following drug solution formulation was prepared.

| Venlafaxine HCl | 1.5 Kg |
|---|---|
| PEG 3350 | 0.075 Kg |
| HPMC | 0.075 Kg |
| Water | 1.2 Kg |

The drug was dissolved in water with slightly heating. PEG was dissolved in the drug solution. The HPMC is dissolved in the drug solution following PEG addition.

EXAMPLE 8

Using the procedure of Example 1 or 2, the following drug solution formulation was prepared.

| Venlafaxine HCL | 1.5 Kg |
|---|---|
| PEG 3350 | 0.05 Kg |
| HPMC | .01 Kg |
| Water | 1.2 Kg |

The drug was dissolved in water with slightly heating. PEG was dissolved in the drug solution. The HPMC is dissolved in the drug solution following PEG addition.

EXAMPLE 9

Using the procedure of Example 1 or 2, the following drug solution formulation was prepared.

| Venlafaxine HCL | 1.5 Kg |
|---|---|
| PEG 3350 | 0.1 Kg |
| HPMC | 0.05 Kg |
| Water | 1.2 Kg |

The drug was dissolved in water with slightly heating. PEG was dissolved in the drug solution. The HPMC is dissolved in the drug solution following PEG addition.

EXAMPLE 10

The following drug solution formulation was prepared.

| Venlafaxine HCL | 1.5 Kg |
|---|---|
| Tween 80 | 0.0075 Kg |
| PEG | 0.3 Kg |
| Water | 1.2 Kg |

The drug was dissolved in water with heating, then PEG and Tween were dissolved in the drug solution, in accordance with the procedures of Example 1 or 2.

The above preferred embodiments are given to illustrate the scope and spirit of the present invention. The embodiments described herein will make apparent to those skilled in the art other embodiments. These other embodiments are within the contemplation of the present invention. Therefore, the present invention should be limited only by the appended claims.

What is claimed is:

1. A pharmaceutical composition in a solid unit dosage form comprised of a water soluble drug prepared by the process comprising:
   (a) preparing a supersaturated drug solution containing a desired amount of drug, which drug solution is completely saturated at a first temperature but which is supersaturated at a second temperature which is below the first temperature;
   (b) coating inert beads with the drug solution, said drug solution being maintained at or below the first temperature but above the second temperature, and said beads are maintained at a second temperature, wherein the second temperature is less than the first temperature and wherein the second temperature is the temperature at which the solution containing the drug is supersaturated; and
   (c) formulating a pharmaceutically effective amount of said drug into a solid unit dosage form.

2. The pharmaceutical composition prepared by the process of claim 1, wherein the supersaturated drug solution comprises the water soluble drug, an aqueous solvent, and polyethylene glycol, said polyethylene glycol being present in an amount ranging from about 2% to about 50% (w/w) on a dry weight basis relative to the water soluble drug.

3. The pharmaceutical composition prepared by the process of claim 1, comprising a pharmaceutically effective amount of a water soluble drug and polyethylene glycol, said polyethylene glycol being present in an amount ranging from about 2% to about 50% (w/w) on a dry weight basis, said water soluble drug and polyethylene glycol being coated onto a pellet in a first coat, said first coat being optionally coated with a second coat comprised of a controlled release polymer.

4. The pharmaceutical composition according to claim 3 wherein the polyethylene glycol has a degree of polymerization greater than about 800.

5. The pharmaceutical composition according to claim 3 wherein the polyethylene glycol has a degree of polymerization greater than about 1400.

6. The pharmaceutical composition according to claim 3 wherein the polyethylene glycol has a degree of polymerization greater than about 3000.

7. The pharmaceutical composition according to claim 3 wherein the polyethylene glycol is present in an amount ranging from about 5% to 30% (w/w) dry weight basis.

8. The pharmaceutical composition according to claim 3 wherein the polyethylene glycol is present in an amount ranging from about 10% to 25% (w/w) dry weight basis.

9. The pharmaceutical composition according to claim 3 wherein the polyethylene glycol is present in an amount about 20% (w/w) dry weight basis.

10. The pharmaceutical composition according to claim 3 wherein the drug is present in a concentration greater than about 40% by weight.

11. The pharmaceutical composition according to claim 3 wherein the drug is present in a concentration greater than about 50% by weight.

12. The pharmaceutical composition according to claim 3 wherein the drug is present in a concentration greater than about 60% by weight.

13. The pharmaceutical composition according to claim 3 wherein a surfactant is additionally present.

14. The pharmaceutical composition according to claim 3 wherein the surfactant is a non-ionic surfactant.

15. The pharmaceutical composition according to claim 3 wherein the surfactant is present in an amount ranging from about 0.1% to about 1% (w/w) on a dry weight basis.

16. The pharmaceutical composition according to claim 3 wherein a controlled release polymer is additionally present, said controlled release polymer being present in a second coat.

17. The pharmaceutical composition according to claim 16 wherein a protective coat is present, said protective coat located between the first coat and the second coat.

18. The pharmaceutical composition according to claim 16 wherein the controlled release polymer is a water insoluble polymer, a water soluble polymer, or an enteric polymer.

19. The pharmaceutical composition according to claim 18 wherein the water soluble polymer is hydroxypropylmethylcellulose, hydroxypropylcellulose, carboxymethyl cellulose, polyvinylpyrolidone, xanthan gum or a mixture thereof.

20. The pharmaceutical composition according to claim 18 wherein the water insoluble polymer is ethylcellulose, acrylic polymer, polymethyl-methacrylate, polyvinylacetate or mixtures thereof.

21. The pharmaceutical composition according to claim 18 wherein the enteric polymer is cellulose acetate phthalate, hydroxypropylmethylcellulose acetate succinate, carboxymethylcellulose, styrene acrylic copolymers, methacrylic copolymers, maleic anhydride copolymers, shellac or mixture thereof.

22. The pharmaceutical composition according to claim 3 wherein the water soluble drug is venlafaxine HCl, metoprolol tartarate, diltiazem salts, pseudoephedrine salts, phenyltolaxamine, brompheniramine maleate or diphenhydramine.

23. The pharmaceutical composition according to claim 3 wherein the water soluble drug is venlafaxine•HCl.

* * * * *